United States Patent
Zhao et al.

(10) Patent No.: US 10,748,659 B2
(45) Date of Patent: Aug. 18, 2020

(54) METHOD AND SYSTEM FOR PREDICTING RISK OF THROMBOSIS

(71) Applicant: Abbott Cardiovascular Systems Inc., Santa Clara, CA (US)

(72) Inventors: Weiying Zhao, Cupertino, CA (US); Dong Li, Sunnyvale, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 1067 days.

(21) Appl. No.: 14/643,154

(22) Filed: Mar. 10, 2015

(65) Prior Publication Data

US 2016/0267243 A1 Sep. 15, 2016

(51) Int. Cl.
*G16H 50/30* (2018.01)

(52) U.S. Cl.
CPC .................................. *G16H 50/30* (2018.01)

(58) Field of Classification Search
None
See application file for complete search history.

(56) References Cited

U.S. PATENT DOCUMENTS

| 2005/0038342 A1* | 2/2005 | Mozayeni | A61B 5/02007 600/454 |
| 2006/0199239 A1* | 9/2006 | Gurbel | C12Q 1/56 435/11 |
| 2015/0278470 A1* | 10/2015 | Bakker | G06F 19/3431 705/2 |

FOREIGN PATENT DOCUMENTS

WO  WO-2007044278 A2 * 4/2007 ............. G01N 33/86

OTHER PUBLICATIONS

"Coronary Atlas for Better Stent Design." Scoop Media, Oct. 14 2014, p. NA. ProQuest. Web. Apr. 3, 2020 . (Year: 2014).*

* cited by examiner

*Primary Examiner* — Lena Najarian
(74) *Attorney, Agent, or Firm* — Womble Bond Dickinson (US) LLP

(57) ABSTRACT

Assessing a risk associated with implantation of a drug delivery device configured to treat blood vessels, is described. Particularly, devices, methods, and systems for assessing the risk of stent thrombosis, prior to implantation, for determining the appropriate stent and/or medication regimen for a particular patient, and continuing to assess the risk of stent thrombosis after implantation, thereby improving the efficacy of the therapy, are described. Other embodiments are described and claimed.

13 Claims, 13 Drawing Sheets

| | |
|---|---|
| AGE ≥65 | 1 |
| GENDER (M) | 1 |
| CURRENT TOBACCO USE | 0 |
| DIABETES Rx | 0 |
| HYPERTENSION Rx | 1 |
| DYSLIPIDEMIA Rx | 0 |
| PRIOR CABG | 0 |
| PRIOR PCI | 0 |
| CCS III | 1 |
| CCS IV | 0 |
| PRIOR MI | 0 |
| PRIOR BRACHYTHERAPY | 0 |
| PRIOR AMI | 0 |
| RENAL INSUFFICIENCY | 0 |
| STROKE | 0 |
| LVEF <30% | 1 |
| # DISEASED VESSELS ≥2) | 1 |

Fig. 9

| | |
|---|---|
| TARGET VESSEL (LAD) | 1 |
| TARGET VESSEL (left main) | 0 |
| TARGET VESSEL (Graft) | 0 |
| PRESENCE OF THROMBUS | 1 |
| HEAVY CALCIFICATION | 1 |
| PRE PROC RVD (mm) | 3.02 |
| PRE PROC DS% <70% | 0 |
| PRE PROC TIMI | 1 |
| TARGET LESION LENGTH ≥22mm | 0 |
| IN STENT RESTENOSIS | 1 |
| BIFURCATION | 0 |
| OSTIAL | 0 |
| LESION CLASS B2/C | 1 |

Fig. 10

| 950 | 904 |
|---|---|
| CLOPIDOGREL | 0 |
| PRASUGREL | 1 |
| TICAGRELOR | 0 |
| DAPT DISCONTINUATION BEFORE 6 MONTHS | 1 |
| ASPIRIN DISCONTINUATION BEFORE 6 MONTHS | 0 |

Fig. 12

| 960 | 904 |
|---|---|
| STENT THROMBOSIS (0-30 days) | 0 |
| STENT THROMBOSIS (30 days-1year) | 1 |
| STENT THROMBOSIS (>1 year) | 0 |

Fig. 13

METHOD AND SYSTEM FOR PREDICTING RISK OF THROMBOSIS

FIELD OF THE DISCLOSED SUBJECT MATTER

The disclosed subject matter relates to assessing the risk associated with implantation of a drug delivery device configured to treat blood vessels. Particularly, the present disclosed subject matter is directed to devices, methods, and systems for assessing the risk of stent thrombosis, prior to implantation, for determining the appropriate stent and/or medication regimen for a particular patient, and continuing to assess the risk of stent thrombosis after implantation, thereby improving the safety of the therapy.

BACKGROUND

A leading cause of mortality within the developed world is cardiovascular disease. Coronary disease is of most concern. Patients having such disease have narrowing in one or more coronary arteries. Generally, however, patients have narrowing in multiple coronary arteries. One treatment for the narrowing is stenting the blood vessel. Stenting involves the placement of a stent at the site of acute artery closure. This type of surgery has proved effective in restoring vessel patency and decreasing myocardial ischemia. However the exposure of currently used metallic stents to flowing blood can result in thrombus formation, smooth muscle cell proliferation and acute thrombotic occlusion of the stent.

Drug eluting stents ("DES") generally result in lower restenosis and revascularization rates as compared to bare metal stents in vessels having a diameter greater than approximately 3.0 mm ("large vessels"). In addition to the challenges associated with large vessel stents, vessels having a diameter of less than 3.0 mm ("small vessels") are clinically and angiographically at a disadvantage to larger vessels due to the inability of the small diameter to accommodate neointimal hyperplasia. These small-vessel DES have not led to significantly reduced late loss diameter or percent diameter stenosis like their large-vessel DES counterparts. The disclosed subject matter is particularly advantageous in that it is applicable to both large and small vessels.

A safety concern associated with drug-eluting stents is the occurrence of stent thrombosis. Dual Antiplatelet Therapy ("DAPT"), e.g., the administration of aspirin plus a second anti-clotting medication such as thienopyridine, is one accepted strategy for minimizing the risk of stent thrombosis. The literature suggests that premature DAPT discontinuation is associated with stent thrombosis. Therefore, to mitigate the risk of stent thrombosis, the current ACC/AHA/SCAI guideline recommends patients who receive a DES should be given aspirin indefinitely and thienopyridine for at least 12 months in the absence of increased risk of bleeding. Unfortunately, in real-world practice, patient non-compliance with DAPT therapy occurs due to adverse events, invasive surgery, patient non-compliance with the prescribed therapy, etc.

Accordingly, despite significant improvements in stent design, implantation equipment and techniques, and anti-platelet therapy, stent thrombosis remains to be one of the major safety concerns with drug-eluting stents. Thus, there remains a need for physicians to fully assess the risk of stent thrombosis, ranging from pre-implantation to post-implantation and medication compliance.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and devices particularly pointed out in the written description and claims thereof, as well as from the appended drawings.

In accordance with an aspect of the disclosed subject matter, a method for assessing and/or predicting risk of stent thrombosis is disclosed including providing one or more variables, the one or more variables comprising a baseline variable associated with a characteristic of a subject; and calculating a risk factor associated with stent thrombosis in the subject based on the one or more variables.

In some embodiments, calculating a risk factor associated with stent thrombosis comprises calculating a risk associated with at least one of early stent thrombosis, late stent thrombosis and very late stent thrombosis.

In some embodiments, the calculating a risk factor associated with stent thrombosis comprises encoding a digital file as a series of variables, the one or more variables comprising a baseline variable associated with a characteristic of a subject; and storing said series of variables in a machine readable medium Some embodiments further comprise classifying said series of variables as predicting a level of risk of stent thrombosis; and providing output indicative of said classification.

Furthermore, some embodiments further comprise receiving a plurality of training series of variables with known risks of stent thrombosis; and modifying said classification module to classify each of said training series of variables according to said known risk of stent thrombosis.

In some embodiments, the baseline variable includes one or more baseline demographic variables. In some embodiments, the one or more baseline demographic variable includes one ore more variables selected from the group consisting of age; gender; current tobacco usage; diabetes-related drug intake; hypertension-related drug intake; dyslipidemia-related drug intake; Coronary Artery Bypass Graft history; percutaneous coronary intervention history; CCS III or IV; MI history; brachytherapy history; Acute Myocardial Infarction history; Renal Insufficiency history; Stroke history; Left Ventricle Ejection Fraction; and Number of Diseased Vessels.

In some embodiments, the baseline variable includes one or more baseline angiographic variables. In some embodiments, the one or more baseline angiographic variables includes one or more variable selected from the group consisting of target vessel; presence of thrombus; degree of calcification; pre-procedure RVD; pre-procedure DS %; pre-procedure TIMI; target lesion length; presence of in-stent restenosis; bifurcation; ostial; ACC/AHA lesion class.

In some embodiments, the method further includes providing a procedural variable associated with implantation of a stent within the subject. In some embodiments, the one or more procedural variables includes at least one variable selected from the group consisting of drug eluting stent type; use of pre dilation; use of post dilatation; maximum balloon pressure; number of treated lesions; number of treated vessels; number of stents implanted; total length stent; bailout stent usage; DAPT loading dose usage.

In some embodiments, providing the one or more variables further includes providing at least one post-procedural variable associated with a characteristic of the subject after stent implantation.

In some embodiments, the at least one post-procedural variable comprises at least one variable selected from the group consisting of a type of non-aspirin DAPT medication, non-aspirin DAPT discontinuation events, and aspirin discontinuation events.

In some embodiments, the at least one post-procedural variable includes at least one variable selected from the group consisting of type of $P2Y_{12}$ receptor inhibitor medication, $P2Y_{12}$ receptor inhibitor discontinuation events, and aspirin discontinuation events.

In accordance with another aspect of the disclosed subject matter, a non-transient computer readable medium is provided, which includes instructions for receiving one or more variables, the one or more variables comprising a baseline variable associated with a characteristic of a subject; instructions for calculating a risk factor associated with stent thrombosis in the subject based on the one or more variables; and instructions for providing an output relating to the risk factor.

In accordance with another aspect of the disclosed subject matter, a system for predicting risk of stent thrombosis is provided which includes an encoding module operable to encode a digital file as a series of variables, the one or more variables comprising a baseline variable associated with a characteristic of a subject; store said series of variables in a machine readable medium; provide said series of variables to a classification module; and a classification module operable to receive said series of variables from said encoding module or said machine readable medium; classify said series of variables as predicting a level of risk of stent thrombosis; and provide output indicative of said classification.

In some embodiments, a training module is provided, which is operable to receive a plurality of training series of variables with known risks of stent thrombosis; modify said classification module to classify each of said training series of variables according to said known risk of stent thrombosis.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and device of the disclosed subject matter. Together with the description, the drawings serve to explain the principles of the disclosed subject matter.

BRIEF DESCRIPTION OF THE DRAWINGS

FIGS. 9-13 are representations of data files useful for encoding and classifying data in accordance with the disclosed subject matter.

DETAILED DESCRIPTION OF THE PREFERRED EMBODIMENT

Reference will now be made in detail to various embodiments of the disclosed subject matter, an example of which is illustrated in the accompanying drawings. The method and corresponding steps of the disclosed subject matter will be described in conjunction with the detailed description of the device.

The methods and system presented herein are particularly useful in providing an evaluation of the potential risks associated with the treatment of blood vessels. In an exemplary embodiment, the methods and system are directed to the risks associated with an intraluminal stent for improving coronary luminal diameter of small vessels in patients with symptomatic heart disease while mitigating risks associated with stent thrombosis.

The term "stent thrombosis" as used herein, is a broad term and is used in its ordinary sense, including, without limitation, a condition that occurs when a blood clot forms on the surface of a stent, raising the risk of blood flow in an artery being reduced or cut off.

The term "artificial neural network," as used herein, is a broad term and is used in its ordinary sense, including, without limitation, to refer to feedforward neural networks, single and multilayer perceptrons, and recurrent neural networks.

Figure 1:
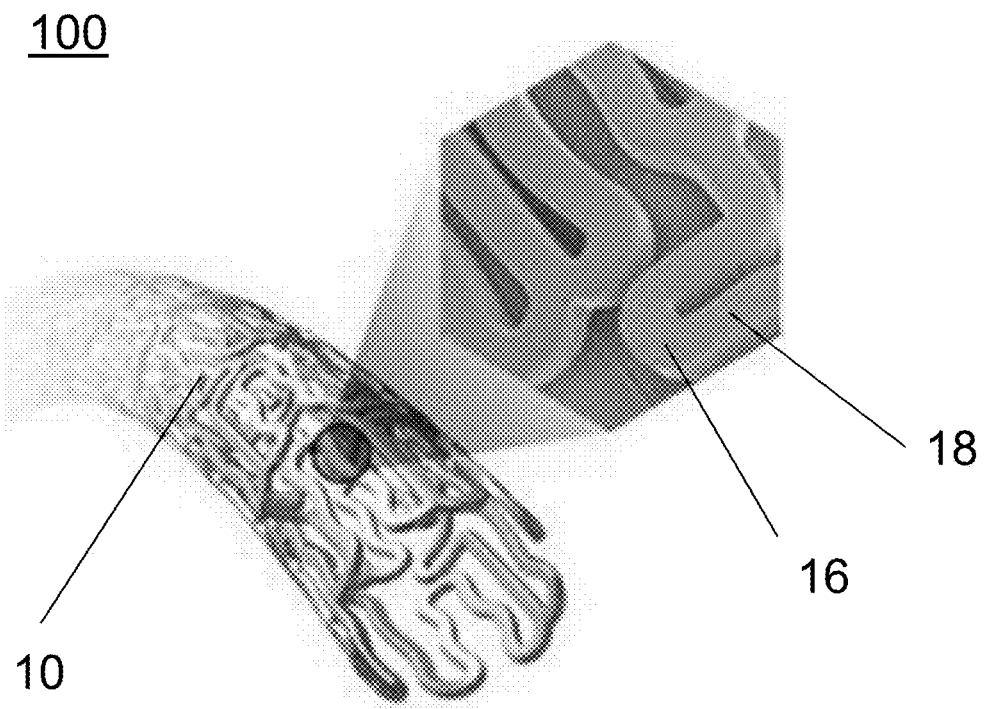
FIG. 1 is a schematic representation of the drug delivery device in accordance with the disclosed subject matter.
Figure 2:
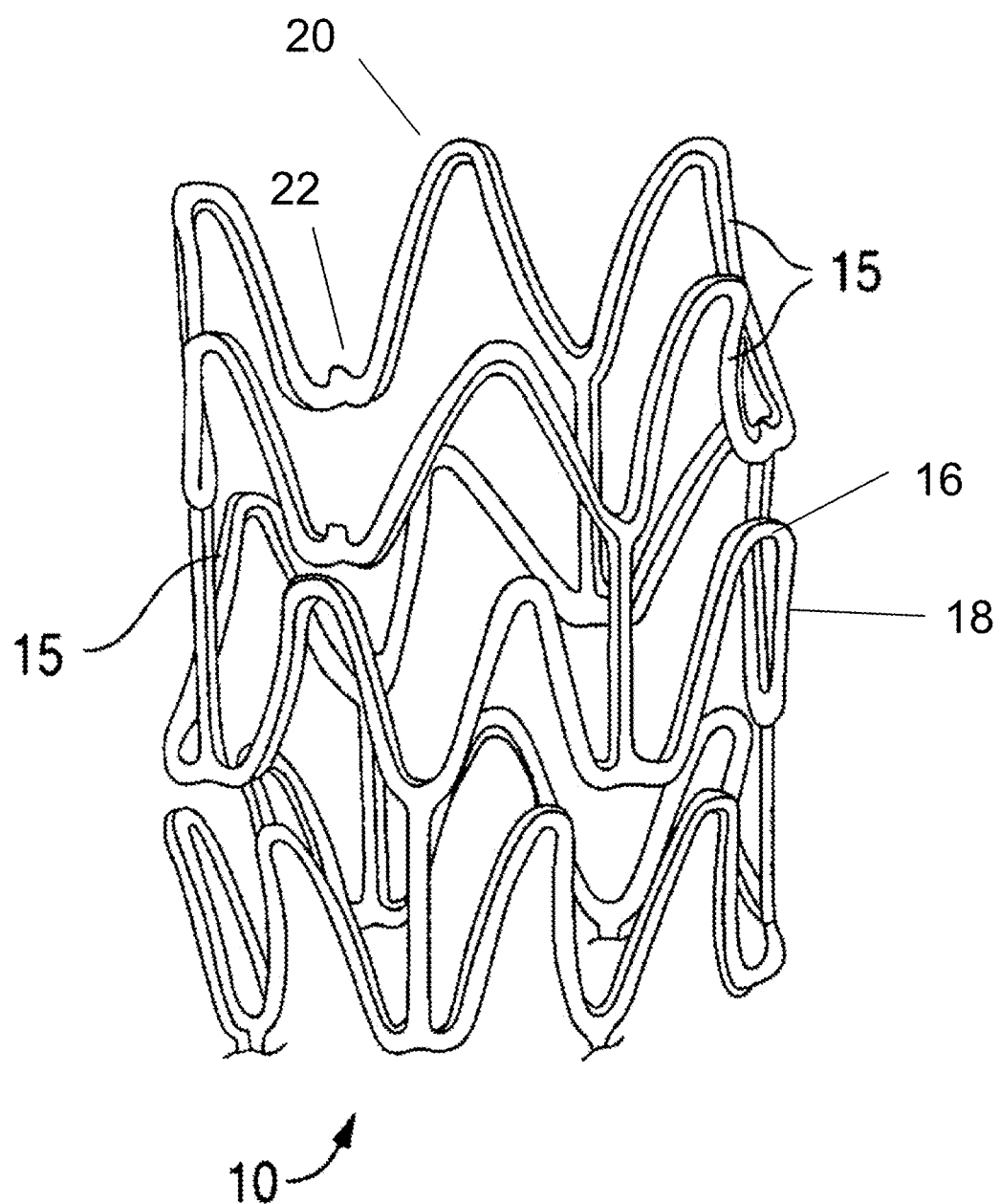
FIG. 2 is a schematic representation of an alternative geometry of a stent in accordance with the disclosed subject matter.
Figure 3:
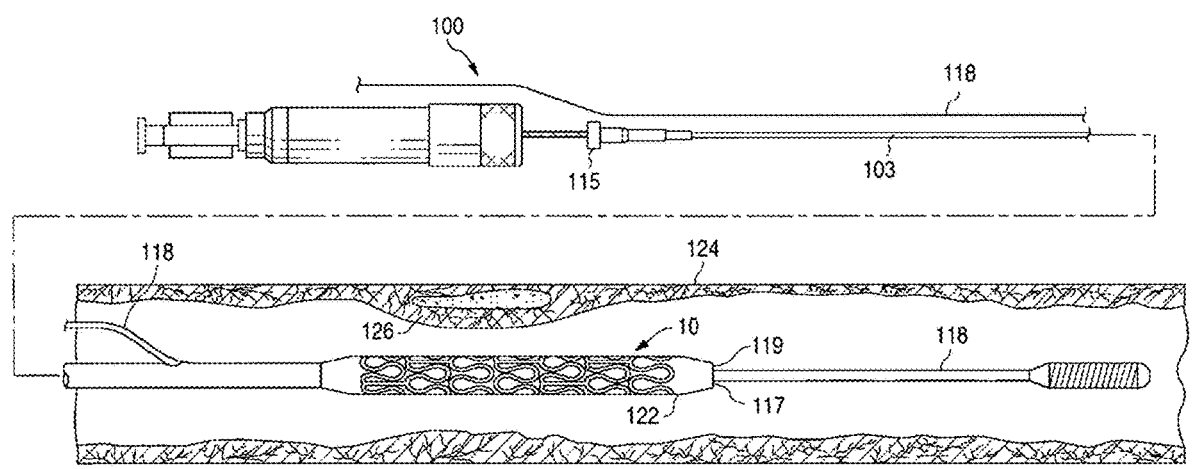
FIG. 3 is a schematic representation of a stent delivery system in accordance with the disclosed subject matter.

For purpose of explanation and illustration, and not limitation, a sample embodiment of a device in accordance with the disclosed subject matter is shown in FIGS. 1-3 and is designated generally by reference character 100. The generally includes an intraluminal base stent, including a stent body 10. As illustrated in the various embodiments shown in FIGS. 1-2, the stent can be configured in a variety of geometries. Although the device and methods associated with the present subject matter may be used in vessels of any size, for purposes of explanation and not limitation, the present disclosure discusses a stent suitable for use in small vessels, e.g., vessels having a diameter of less than or equal to approximately 3.0 mm and an axial length of approximately 12 mm. Prior to deployment the stent is crimped on a balloon, or other suitable expandable device. Crimping can be performed by pressurizing the balloon while the stent is radially compressed onto the balloon with a crimping apparatus. Once the stent has reached its radially compressed configuration, the pressure within the balloon can be released, while an inward crimping force exerted on the stent by the crimping apparatus is maintained. After a dwell time, the inward crimping force can be discontinued, and the balloon and crimped stent are removed from the crimping apparatus. As a result of the crimping process, balloon material extends radially outward through interstices of the stent to facilitate stent retention on the balloon while advancing the stent delivery catheter through a vessel lumen.

In some embodiments, the expanded diameter of the stent ranges from about 2.25 mm at lower balloon inflation pressures (e.g., about 8 atm) to about 2.59 mm at higher balloon inflation pressures (e.g., about 16 atm). In various embodiments, the base stent is designed for use in small vessels having diameters of greater than or equal to approximately 2.25 mm to 2.5 mm. The stent body 10 is preferably but not necessarily balloon expandable and may be fabricated from any suitable metallic material including, e.g., stainless steel, tantalum, nickel-titanium, cobalt-chromium, titanium, shape memory and superelastic alloys, and the noble metals such as gold or platinum, as described in U.S. Pat. No. 6,939,373, which is herein incorporated by reference in its entirety. Alternatively, a self-expanding stent can be employed wherein the stent automatically expands at the desired location within the lumen by retracting a sheath on the delivery catheter. In some embodiments, the stent body is fabricated from L-605 cobalt chromium (CoCr) alloy. In other embodiments, the stent body 10 can be described more particularly as having a series of interconnected strut members which define a plurality of first peaks, second peaks, and valleys disposed therebetween. Although the stent is not divided into separate elements, for ease of discussion references to peaks and valleys is appropriate. The number of peaks and valleys can vary in number for each ring depending upon the application. Thus, for example, if the stent is to be implanted in a coronary artery, a lesser number of peaks and valleys are required than if the stent is implanted in a peripheral artery, which has a larger diameter than a coronary artery.

Such a small-vessel stent is used in patients who have narrowing in small coronary arteries that are greater than or equal to 2.25 mm to less than or equal to 2.50 mm in diameter and where the affected length of the artery is less than or equal to 28 mm long.

As shown in FIGS. 1-2, stent body 10 is made up of a plurality of cylindrical rings 15 which extend circumferentially around the stent when it is in a tubular form. The stent has a delivery catheter outer shaft diameter of 0.032" distally and 0.026" proximally. Each cylindrical ring has a cylindrical ring proximal end and a cylindrical ring distal end. Typically, since the stent is laser cut from a tube there are no discreet parts such as the described cylindrical rings and links. However, it is beneficial for identification and reference to various parts to refer to the cylindrical rings and links and other parts of the stent as follows.

Each cylindrical ring 15 defines a cylindrical plane which is a plane defined by the proximal and distal ends of the ring and the circumferential extent as the cylindrical ring travels around the cylinder. Each cylindrical ring includes cylindrical outer wall surface which defines the outermost surface of the stent, and cylindrical inner wall surface which defines the innermost surface of the stent. The cylindrical plane follows the cylindrical outer wall surface.

In keeping with the invention, an undulating link is positioned within cylindrical plane. The undulating links connect one cylindrical ring 15 to an adjacent cylindrical ring 15 and contribute to the overall longitudinal flexibility to the stent due to their unique construction. The flexibility of the undulating links derives in part from curved portion 16 connected to straight portions 18. In the exemplary embodiment shown in FIG. 1, the straight portions are substantially perpendicular to the longitudinal axis of the stent. Thus, as the stent is being delivered through a tortuous vessel, such as a coronary artery, the curved portions 16 and straight portions 18 of the undulating links will permit the stent to flex in the longitudinal direction which substantially enhances delivery of the stent to the target site. The number of bends and straight portions in a link can be increased or decreased from that shown, to achieve differing flexibility constructions. With the straight portions being substantially perpendicular to the stent longitudinal axis, the undulating link acts much like a hinge at the curved portion to provide flexibility. A straight link that is parallel to the stent axis typically is not flexible and does not add to the flexibility of the stent.

The stent body 10 can be described more particularly as having a plurality of peaks 20 and valleys 22, as shown in FIG. 2. Although the stent is not divided into separate elements, for ease of discussion references to peaks and valleys is appropriate. Each of the cylindrical rings 15 has a plurality of peaks 20 which have struts 18 attached to an apex. The struts can be either curved or straight depending upon the particular application.

The stent body 10 can be made in many ways. One method of making the stent is to cut a thin-walled tubular member, and to remove portions of the tubing in the desired pattern for the stent, leaving the desired pattern of struts and connectors (if present) to define the stent body. In some embodiments, the tubing is cut in the desired pattern by means of a machine-controlled laser as is well known in the art. In some embodiments, the struts have a thickness of less than approximately 110 μm. In a specific embodiment, the struts have a thickness of 81 μm.

In some embodiments, the base stent is coated with active and inactive ingredients. The inactive ingredients include polymers, e.g., poly(N-acetylglucosamine) (Chitin), Chitosan, poly(3-hydroxyvalerate), poly(D,L-lactide-co-glycolide), poly(1-lactide-co-glycolide) poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrin glue, fibrinogen, cellulose, starch, collagen and hyaluronic acid, elastin and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), poly(vinylidene fluoride), poly(vinylidene fluoride-co-hexafluoropropylene), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates including tyrosine-based polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, carboxymethyl cellulose, fullerenes and lipids. In a specific embodiment, the inactive ingredients are the polymers poly n-butyl methacrylate (PBMA) and PVDF-HFP, which is comprised of vinylidene fluoride and hexafluoropropylene monomers. PVDF-HFP is a non-erodible semi-crystalline random copolymer with a molecular weight of 254,000 to 293,000 daltons. PBMA is a homopolymer with a molecular weight of 264,000 to 376,000 daltons.

The active ingredient may include a therapeutic agent that can include any substance capable of exerting a therapeutic or prophylactic effect. Examples of therapeutic agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin I1, actinomycin X1, and actinomycin C1. The bioactive agent can also fall under the genus of antineoplastic, anti-inflammatory, antiplatelet, anticoagulant, antifibrin, antithrombin, antimitotic, antibiotic, antiallergic and anti-oxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, thienopyridine, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin.

In a specific embodiment the active agent is everolimus. Everolimus, developed by Novartis Pharma AG, is a proliferation signal inhibitor, or mTOR inhibitor. It is a semi-synthetic macrolide immunosuppressant, synthesized by chemical modification of rapamycin (sirolimus). Everolimus has been shown to inhibit in-stent neointimal growth in coronary vessels following stent implantation due to its anti-proliferative properties.

In one embodiment, PBMA, which adheres well with metallic materials and other polymers, is used as a primer to coat the base stent. PVDF-HFP is used as a drug matrix that is mixed with everolimus. The PVDF-HFP/everolimus mixture is adhered to the surface of the PBMA coated stent. In a specific embodiment, this PVDF-HFP/everolimus mixture comprises 83% polymer and 17% everolimus. The thickness of the polymer coating is less than approximately 10 μm. In a specific embodiment, the thickness of the polymer coating is 7.1 μm. The concentration of the everolimus in the copolymer is about 50 μg/cm$^2$ to about 150 μg/cm$^2$. In a specific embodiment the concentration of the everolimus in the copolymer is 100 μg/cm$^2$. Systems and methods for coating stents are disclosed in U.S. Pat. No. 8,003,157, which is herein incorporated by reference in its entirety.

FIG. 3 depicts stent 10 mounted on a stent delivery assembly 100 which is used to deliver the stent and implant it in an artery 124, peripheral artery, or other vessel or lumen within the body. Stent delivery assembly 100 shown in FIG. 3 includes a catheter 103 which has a proximal end 115 and a distal end 117. The stent delivery assembly is configured to advance through the patient's vascular system by advancing over a guide wire by any of the well known methods. Stent delivery assembly 100 as depicted in FIG. 3 includes a port where a guide wire 118 will exit the catheter. The distal end of the guide wire exits catheter distal end 119 so that the catheter advances along the guide wire on a section of the catheter between the port and the catheter distal end. Stent 10 is mounted on an expandable member 122 (balloon) and is crimped tightly thereon so that stent 100 and expandable member 122 present a low profile diameter for delivery through the coronary arteries. In a typical procedure to implant stent 10, guide wire 118 is advanced through the patient's vascular system by well known methods so that the distal end of the guide wire is advanced past a diseased area 126. Thereafter, stent delivery assembly 100 is advanced over the guide wire so that the stent assembly is positioned in the target area. Expandable member or balloon 122 is inflated by well known means so that it expands radially outwardly and in turn expands the stent radially outwardly until the stent is apposed to the vessel wall. The expandable member is then deflated and the catheter withdrawn from the patient's vascular system.

Radiopaque balloon markers may be used to position the stent across the lesion. Angiography may be used to confirm stent position. If the position of the stent is not optimal, it should be carefully repositioned or removed. The balloon markers indicate both the stent edges and the balloon shoulders. Expansion of the stent should not be undertaken if the stent is not properly positioned in the target lesion. Then, the rotating hemostatic valve should be tightened.

Next, the stent may be deployed. In some embodiments, the stent is deployed slowly by pressurizing the delivery system in 2 atm increments, every 5 seconds, until completely expanded. Accepted practice generally targets an initial deployment pressure that would achieve a stent inner diameter ratio of about 1.1 times the reference vessel diameter. In some embodiments, pressure is maintained for 30 seconds. If necessary, the delivery system can be repressurized or further pressurized to assure complete apposition of the stent to the artery wall. The entire lesion and balloon treated area (including dissections) should be covered with the stent, allowing for adequate stent coverage into healthy tissue proximal and distal to the lesion. The balloon is then deflated by withdrawing the inflation medium (e.g., liquid, air or some other gas) from the inflation device for 30 seconds.

Post procedure, when crossing a newly a newly deployed stent with an intravascular ultrasound (IVUS) catheter, a coronary guide wire, a balloon catheter or delivery system, care should be exercised to avoid disrupting the stent placement, apposition, geometry, and/or coating. Additionally, it may be desirable to provide antiplatelet therapy post-procedure. Patients who require early discontinuation of antiplatelet therapy (e.g., secondary to active bleeding) should be monitored carefully for cardiac events. At the discretion of the patient's treating physician antiplatelet therapy should be restarted as soon as possible.

Despite major improvements in antiplatelet therapy, stent design and stent implantation techniques, stent thrombosis remains to be the one of the major safety concerns with stent implantation, and drug-eluting stents in particular. The disclosed subject matter provides a system and corresponding method that allows physicians to assess the risk of stent thrombosis before the stent implantation to decide on the intervention choice, i.e., whether a bare metal stent or drug eluting stent is most appropriate for a particular patient. The disclosed subject matter also allows physicians to assess antiplatelet medication regimen (type, duration, etc.). Further, another aspect of the disclosed subject matter allows physicians to continue to assess the risk of stent thrombosis based on the procedural data and medication compliance during follow up after stent implantation.

Figure 4:
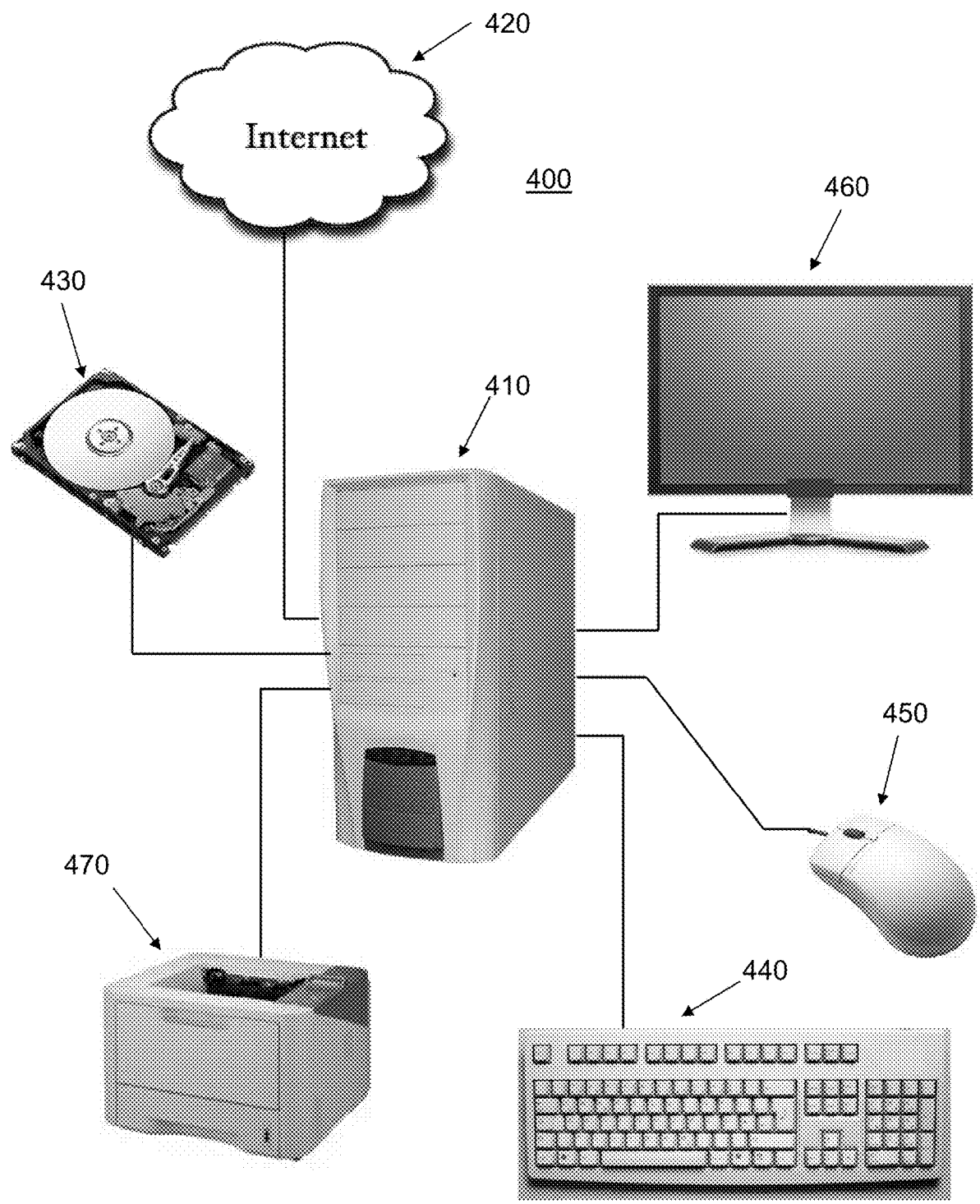
FIG. 4 is a schematic representation of a system for predicting a risk of thrombosis in accordance with the disclosed subject matter.

FIG. 4 illustrates an exemplary embodiment of a system 400 in accordance with the disclosed subject matter. In an exemplary embodiment of the disclosed subject matter, a system and corresponding method is provided which receives as inputs key baseline, procedural and post-procedural variables as covariates. System 400 includes a CPU 410, which may be configured as a distributed system including connection to the internet 420. The CPU 410 includes storage of a database, e.g., on a hard drive 430 or other storage device. The database may include the risk assessment model for determining the risk of thrombosis discussed herein. Further, the database may contain information regarding profile of certain users about to undergo treatment. The system 400 also includes input devices for allowing a user to provide the analysis variables, e.g., keyboard 440 and mouse 450. Output devices include a display 460 and printer 470 for displaying a user interface, as discussed herein, or for providing the risk assessment output information. In some embodiments, the system 400 is provided in an integrated apparatus, such as a laptop, a smartphone, a PDA, or a tablet. 10. A non-transient computer readable medium is provided, which can be stored in non-transient memory on the CPU 410, on the hard drive 430, or on the internet and accessed by the CPU. The non-transient memory includes instructions for receiving one or more variables, the one or more variables including a baseline variable associated with a characteristic of a subject; instructions for calculating a risk factor associated with stent thrombosis in a subject based on the one or more variables; and instructions for providing an output relating to the risk factor.

An exemplary embodiment for a user interface 500 is illustrated in FIGS. 5-8. Such user interface may be displayed on a monitor or other display. The user interface 500 allows the user to input a number of variables for the calculation of the risk of stent thrombosis. The user interface 500 includes information, e.g., regarding the patient, the date of the evaluation and the healthcare provider. Such information may be displayed in a banner portion 510 or other portion of the display. Other identifying information may be displayed and/or stored, e.g., healthcare facility, insurance information, etc.

Figure 5:
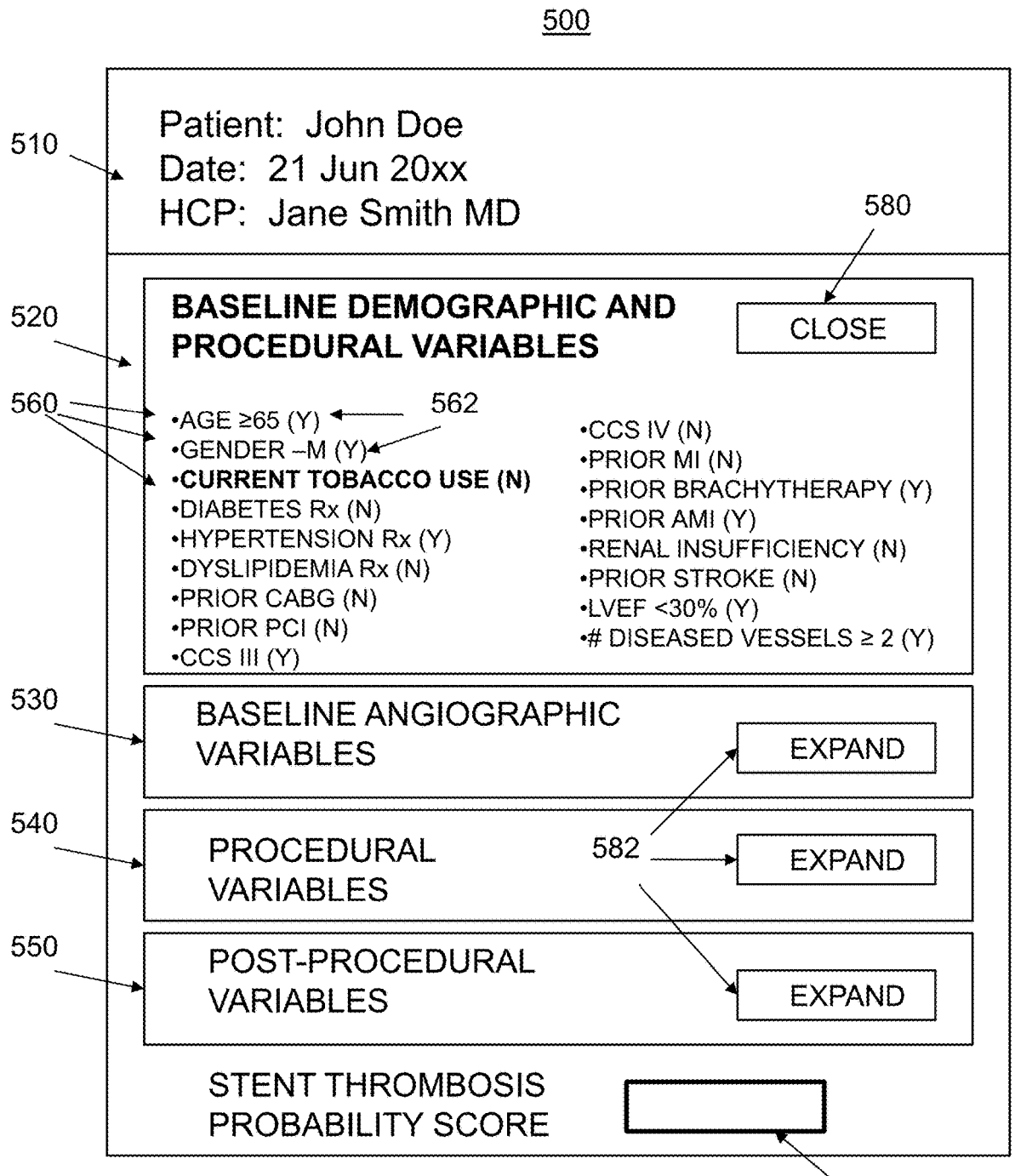
FIGS. 5-8 are representations of a user interface in accordance with the disclosed subject matter.
Figure 6:
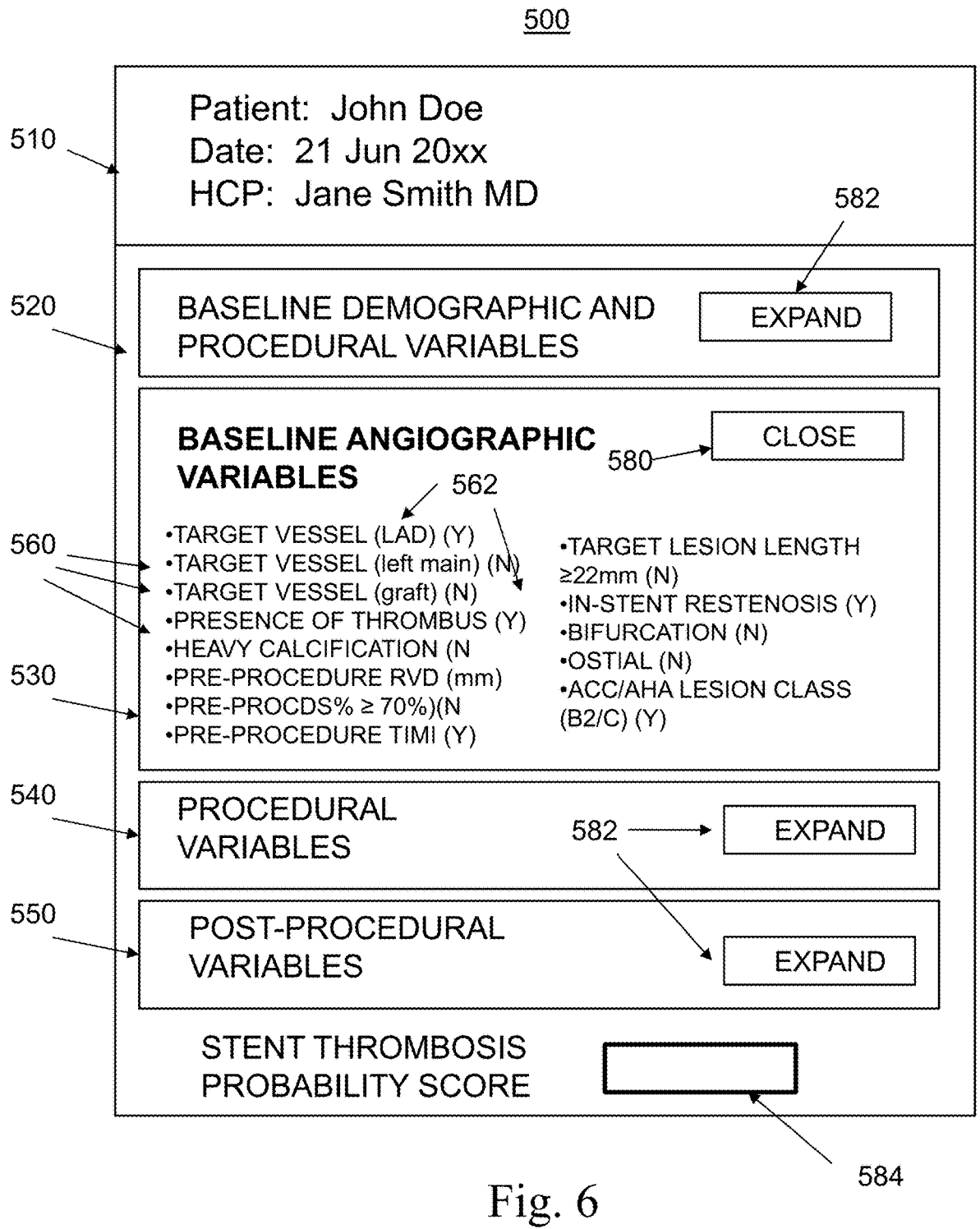
Figure 7:
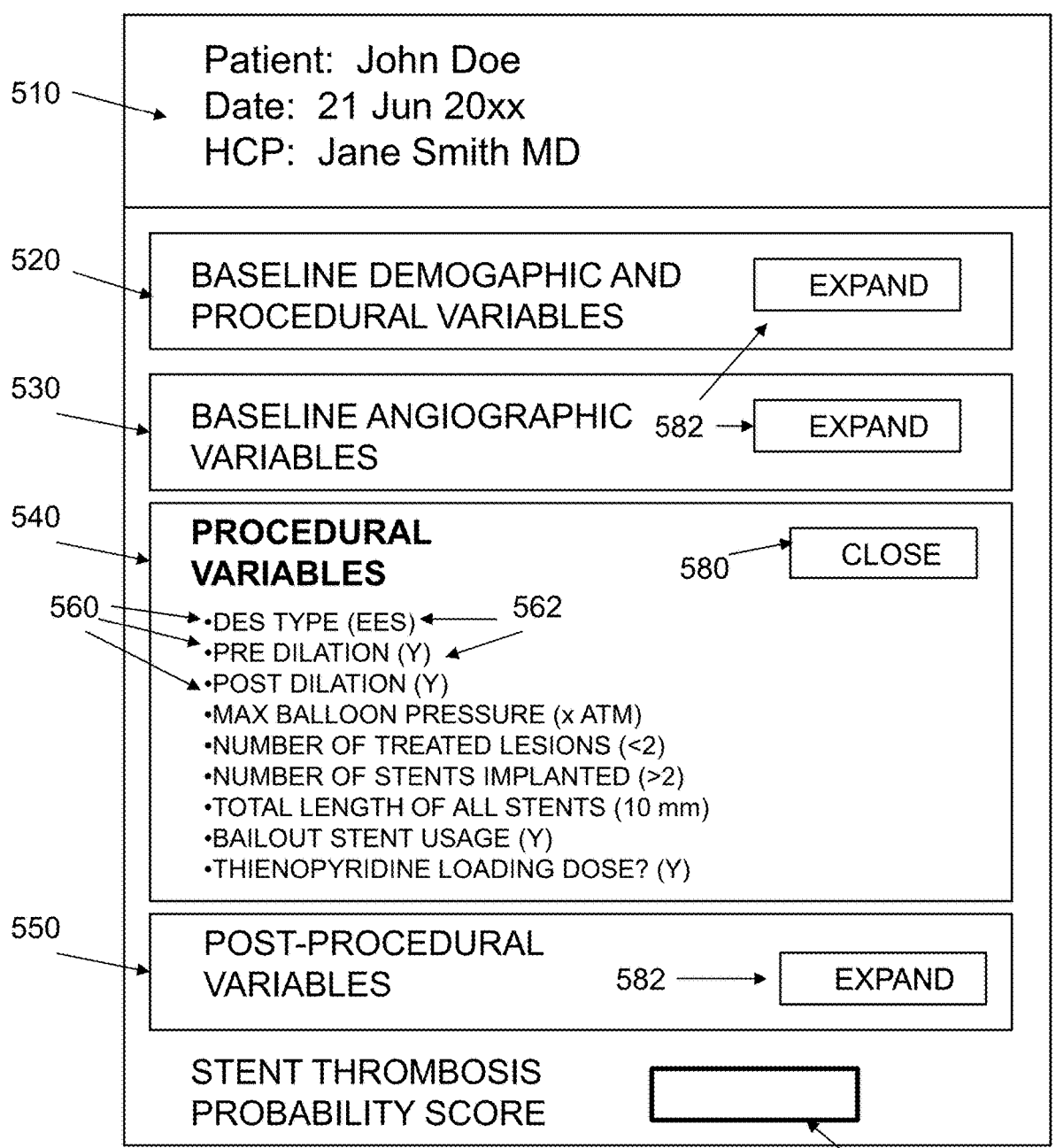
Figure 8:
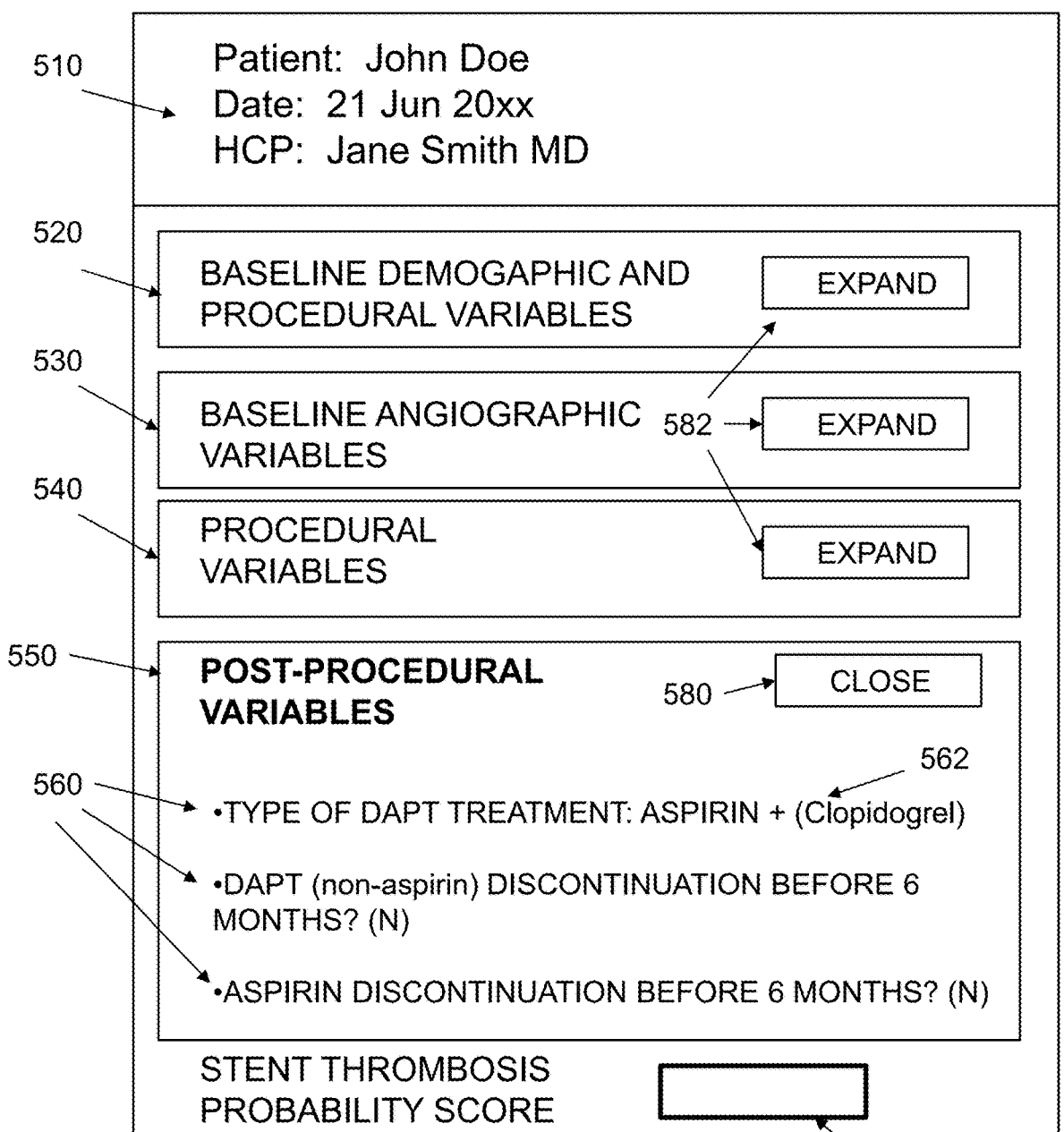

According to the exemplary embodiment, the user is provided with a number of sub-frames 520, 530, 540, 550 on the display, each relating to a category of variables for determining the risks associated with stent thrombosis. Each category contains a number of parameters 560, e.g., age, gender, current tobacco use, diabetes requiring medication ("Diabetes Rx"), hypertension requiring medication ("Hypertension Rx"), etc. The list of variables 560 for a particular category may be viewed by selecting the category. (An "expand" 580 button is provided for this purpose.) When the user has completed entering the variables associated with the category, the variables may be hidden from display. (A "close" button 590 is provided for this purpose.) In some embodiments, all categories 520, 530, 540, and 540 and associated variable 560 may be visible concurrently. The variables may be organized into several categories: Baseline demographic and procedural (or clinical) variables 520 (FIG. 5); Baseline angiographic variables 530 (FIG. 6); Procedural variables 540 (FIG. 7); and Post-procedural variables 550 (FIG. 8). In some embodiments, the particular selections 562 of each of the variables 560 is displayed on the user interface 500, e.g., age (<65), gender (Male), current tobacco use (No), diabetes requiring medication (Yes), hypertension requiring medication (No), etc. The probability score for stent thrombosis 584 is displayed on the user interface 500. The probability score can be represented by three outcome variables, including early stent thrombosis (0-30 days), late stent thrombosis (30 days-1 year) and very late stent thrombosis (>1 year). Alternatively, a composite probability score can be represented which accounts for the risk of stent thrombosis irrespective of the time of occurrence.

The baseline variables, e.g., baseline demographic and clinical variables, are used to predict risk of stent thrombosis before stent implantation. For purposes of illustration and not limitation, some examples of such baseline (or clinical) variables are described herein. For example, the subject patient's age (e.g., whether the patient is 65 years old or older or younger than 65 years old); gender; current tobacco use; whether the patient is a diabetic and currently under a prescription drug regimen, etc. An exemplary listing of baseline demographic and clinical variables is provided in Table 1

TABLE 1

| | | |
|---|---|---|
| Age ≥65 years old | Yes | No |
| Gender Male | Yes | No |
| Current tobacco use | Yes | No |
| Patient is diabetic and currently under a prescription drug regimen | Yes | No |
| Patient has hypertension and currently under a prescription drug regimen | Yes | No |
| Patient has dyslipidemia and currently under a prescription drug regimen | Yes | No |
| Prior CABG | Yes | No |
| Prior PCI (percutaneous coronary intervention) history | Yes | No |
| CCS III or IV angina class | Yes | No |
| Prior myocardial infarction (MI) history | Yes | No |
| Prior brachytherapy history | Yes | No |

TABLE 1-continued

| | | |
|---|---|---|
| Prior AMI (acute myocardial infarction) history | Yes | No |
| Prior Renal Insufficiency history | Yes | No |
| Prior Stroke history | Yes | No |
| Left ventricle ejection fraction (LVEF) ≥30% | Yes | No |
| Number of Diseased Vessels ≥2 | Yes | No |

The baseline variables can also include baseline angiographic variables. For purposes of illustration and not limitation, some examples of such baseline angiographic variables include certain parameters of the target vessel of the patient, such as LAD vs. others; left main vs. others; graft vs. others. Some additional examples of baseline angiographic variables include whether thrombus has been detected; the degree of calcification; pre procedure reference vessel diameter (RVD); pre procedure diameter of stenosis (DS %) (e.g., whether greater or less than a 70% threshold); pre procedure thrombolysis in myocardial infarction grade (TIMI); Target Lesion Length (e.g. whether greater or less than a threshold of 22 mm); presence of any in-stent restenosis; bifurcation of the vessels for the procedure; Ostial; ACC/AHA Lesion Class (B2/C vs. A/B1). An exemplary listing of baseline demographic and clinical variables is provided in Table 2

TABLE 2

| | | |
|---|---|---|
| Target vessel: LAD | Yes | No |
| Target vessel: Left Main | Yes | No |
| Target vessel: Graft | Yes | No |
| Presence of thrombus | Yes | No |
| Heavy calcification | Yes | No |
| Pre procedure RVD | Mm | |
| Pre procedure DS % ≥70% | Yes | No |
| Pre procedure TIMI ≥1 | Yes | No |
| Target lesion length ≥22 mm | Yes | No |
| In-stent Restenosis? | Yes | No |
| Bifurcation? | Yes | No |
| Ostial? | Yes | No |
| ACC/AHA Lesion Class B2/C | Yes | No |

After procedure is completed, baseline and procedural variables can be combined to predict risk of stent thrombosis. For purposes of illustration and not limitation, some examples of such procedural variables include the type of stent, bare metal stent (BMS), bioabsorbable (BVS), drug eluting stent (DES) (e.g., everolimus-eluting stents (EES) vs. paclitaxel-eluting stent (PES) vs. sirolimus-eluting stent (SES) vs. zotarolimus-eluting stent (ZES)); whether the patient was subject to any pre-dilation procedures; whether the patient was subject to any post-dilation procedures; the maximum balloon pressure; the number of treated lesions (e.g., whether greater or less than a threshold of 2); the number of treated vessels (e.g., whether greater or less than a threshold of 2); the number of stents implanted (e.g., whether greater or less than a threshold of 2); the total length of all stents; whether "bailout" stenting was used; dual-antiplatelet therapy (DAPT), e.g., thienopyridine loading dose use (e.g., clopidogrel or prasurgrel). An exemplary listing of procedural variables is provided in Table 3.

TABLE 3

| | | |
|---|---|---|
| Bare Metal Stent (BMS) | Yes | No |
| Bioabsorbable Stent (BVS) | Yes | No |
| Type of DES (EES) | Yes | No |
| Type of DES (PES) | Yes | No |
| Type of DES (SES) | Yes | No |
| Type of DES (ZES) | Yes | No |

TABLE 3-continued

| | | |
|---|---|---|
| Patient subject to pre-dilation procedures | Yes | No |
| Patient subject to post-dilation procedures | Yes | No |
| Maximum balloon pressure | Range atm | |
| Number of treated lesions ≥2 | Yes | No |
| Number of stents implanted ≥2 | Yes | No |
| Total length of all stents ≥10 mm | Yes | No |
| Bailout stent usage | Yes | No |
| DAPT Loading Dose Use | Yes | No |

During patient follow up, post-procedural variables can be added in this model to predict stent thrombosis. For purposes of illustration and not limitation, some examples of such procedural variables include the details of DAPT: the type of $P2Y_{12}$ receptor inhibitor (e.g., clopidogrel or prasurgrel or ticagrelor or others); whether $P2Y_{12}$ receptor inhibitor was discontinued (e.g., whether discontinued before a threshold of 6 months); whether aspirin use was discontinued (e.g., whether discontinued before a threshold of 6 months). Some additional variables which can be factored into the model include whether discontinuation was permanent or just a temporary interruption as well as the frequency, timing and duration of such interruptions. Furthermore, in some embodiments the model can consider whether the patient is on one therapeutic regime where there is an interruption or discontinuation of a second therapeutic regimen (e.g., is patient on aspirin while being off thienopyridine, and vice versa). Additionally, or alternatively, the disclosed subject matter can receive an input for the time (e.g. three months) when a given drug was discontinued. This can be advantageous since the threshold value may be different for a given stent, this configuration allows for the threshold to be built into the algorithm for calculating risk of thrombosis.

In accordance with another aspect of the disclosed subject matter, the model will be an automatic system. For example, the parameters being entered into each of the variable groups described above, e.g., baseline demographic and procedural (or clinical) variables 520; baseline angiographic variables 530; procedural variables 540; and post-procedural variables 550, may be entered into an on-going patient profile. When the risk assessment is desired, the variables may be automatically entered into the risk model.

With data entered for each variable, a probability score of stent thrombosis is determined and displayed. In some embodiments, a neural network is provided to determine the probability score. In the present disclosure, several sets of input nodes are provided, e.g., one set of nodes for each of baseline demographic and procedural variables 520; baseline angiographic variables 530; procedural variables 540; and post-procedural variables 550, with several input nodes in each set as described hereinabove, e.g., Tables 1-3 and as described for post-procedural variables. In operation, each node of the input layer is supplied with an input numeric value, e.g., a binary value.

In the neural network, connections are provided from the input layer to a hidden layer, e.g., from each node in the input layer to each node in the hidden layer, having several nodes. Each node of the input layer transmits its input value over each of its outgoing connections to the nodes of the hidden layer. Each of connections has an associated weight. The weight value of each of connections is applied to the input value, usually by multiplication of the weight with the input. Each node of the hidden layer applies a function to the incoming weighted values. In some embodiments, a sigmoid function is applied to the sum of the weighted values, although other functions are known in the art.

Connections are provided from the hidden layer to the output layer, e.g., from each node of the hidden layer to each node of the output layer. In an exemplary embodiment, the output layer includes one or more output nodes. The results of the function applied by each node of hidden layer are transmitted along connection to each node of the output layer. Each of connections has an associated weight. The weight value of each of connections is applied to the value, usually by multiplication of the weight with the value. Each node of the output layer receives these weighted values, which comprise the output of the neural network.

In one embodiment, there is at least one output node of the output layer that corresponds to the risk of early stent thrombosis (ST). The output values range from 0 to 1, a value of 1 indicating the high risk of early ST, 0 indicating a low risk of early ST, and intermediate values indicating a moderate risk of early ST. Other output nodes can correspond to late ST and very late ST. One of skill in the art would recognize that a different range of values could be selected while still achieving the results of the present disclosure.

The neural network can be trained according to methods known in the art to determine the weights associated with connections between the input layer and the hidden layer and between the hidden layer and the output layer. In a training process, available data regarding the incidence of ST among patients and associated information about the patients is provided to the input layer of neural network. For example, studies of clinical events, such as ST, include demographic, clinical and procedural variables. See, e.g., Naidu et al., "Contemporary Incidence and Predictors of Stent Thrombosis and Other Major Adverse Cardiac Events in the Year After XIENCE V Implantation," *JACC*, Vol. 5, No. 6, 2012.

Figure 11:
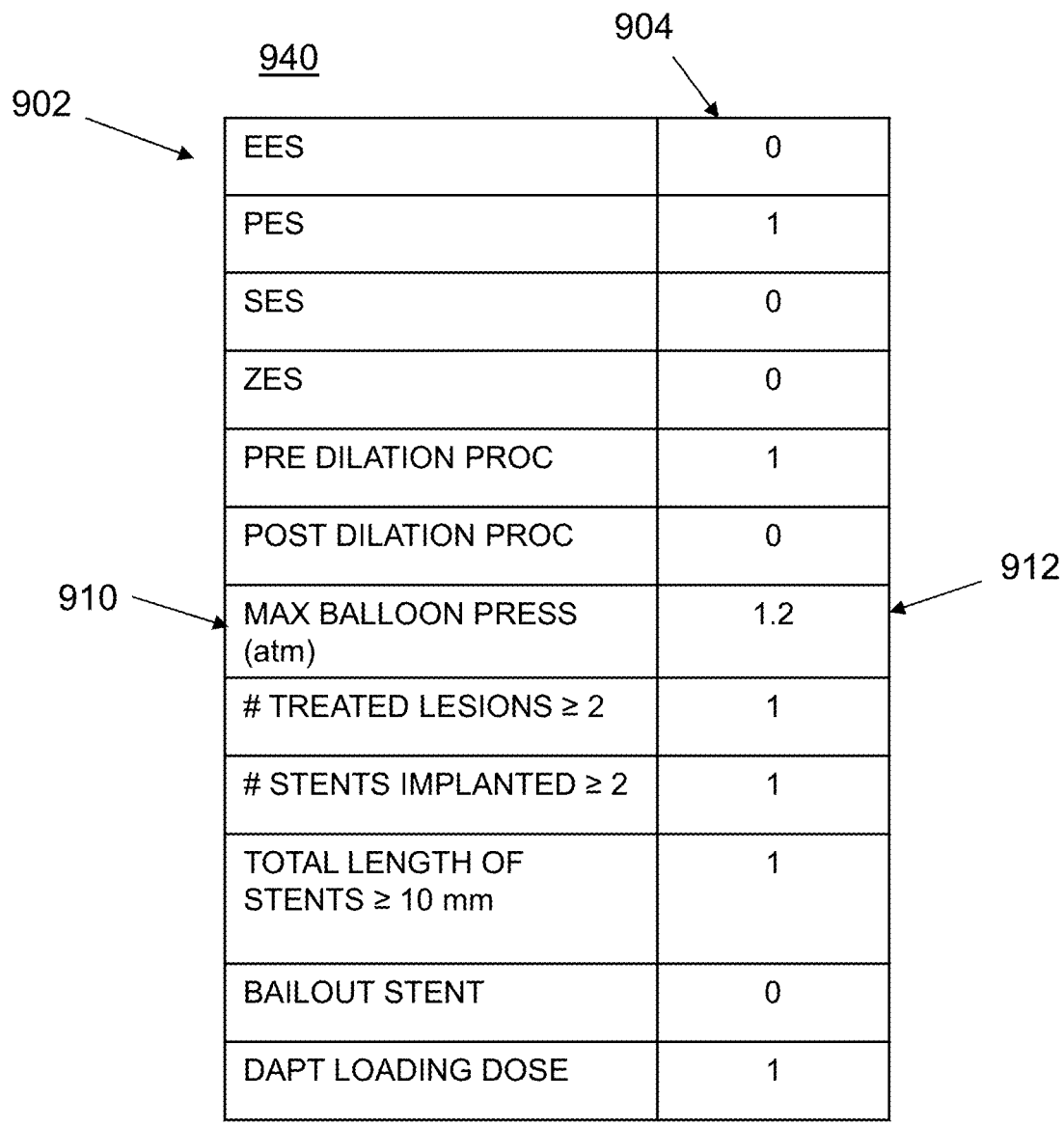

The user interface as described above with respect to FIGS. 5-8 can be used to enter the data from clinical studies in order to train the neural network. As illustrated in FIGS. 9-14, a digital file is represented for encoding the data. For example, data file 920 represents the data corresponding to the baseline demographic and procedural (or clinical) variables 520. Each parameter is denoted as variable 902, and its corresponding value 904. In some embodiments, the value can be represented as a binary value, e.g., "high" or "low." Similarly, data file 930 represents data for baseline angiographic variables 530 (FIG. 10), data file 940 represents data for procedural variables 540 (FIG. 11); and data file 550 represents data for post-procedural variables 550 (FIG. 12). As illustrated in FIGS. 10-11, the selected variable 910 may have a corresponding numerical value 912. An additional data file 960 reflect the outcome for the particular patient, e.g., occurrence of early stent thrombosis (0-30 days), late stent thrombosis (30 days-1 year); and very late stent thrombosis (later than 1 year).

Entry of the data into the training module may be performed by creating data files for each historical procedure and outcome for each patient. Alternatively, data entry from large clinical studies may be entered into the data base in an automated fashion.

Figure 14:
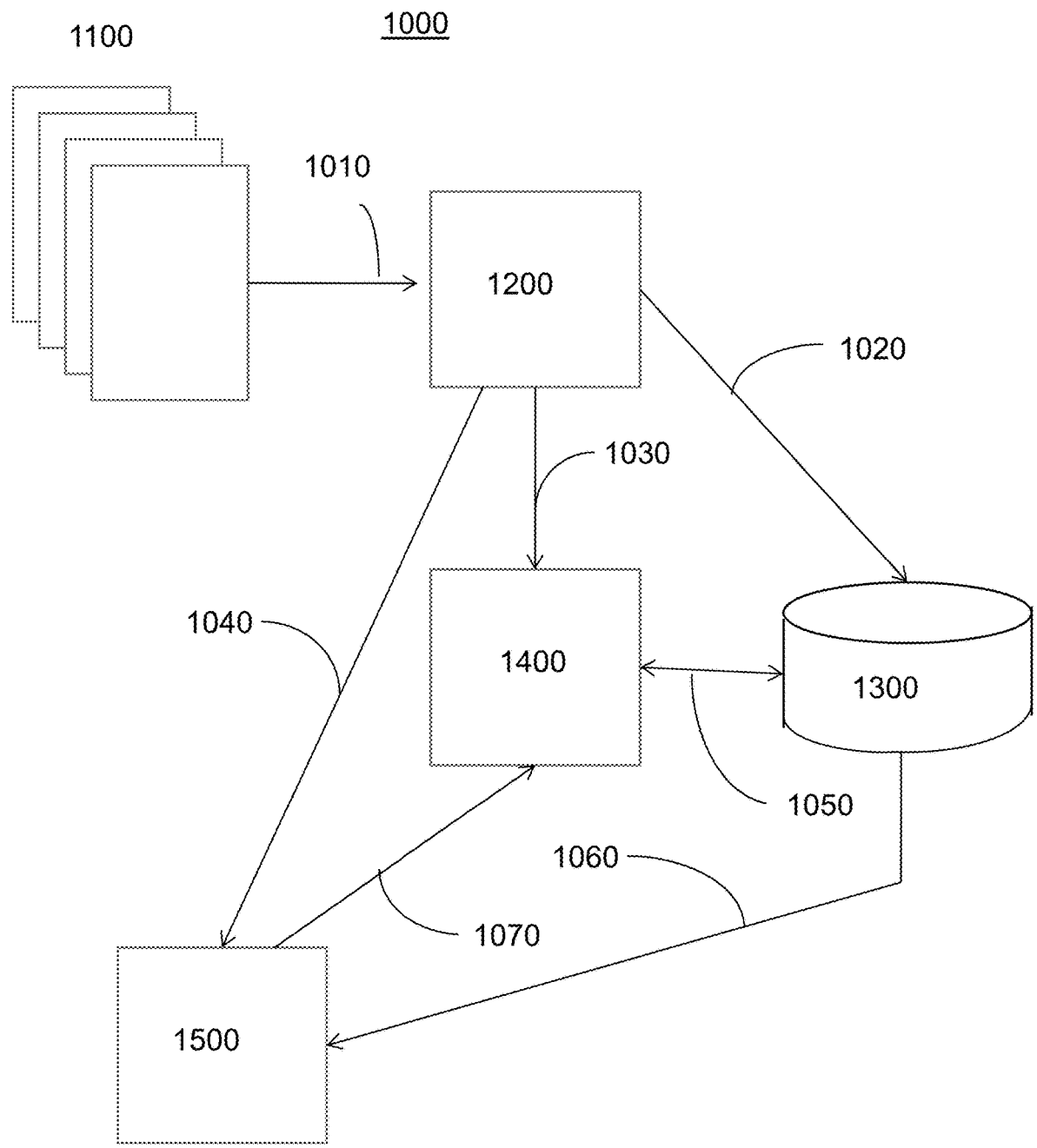
FIG. 14 is a schematic representation of a system for predicting a risk of thrombosis in accordance with the disclosed subject matter.

FIG. 14 illustrates an exemplary system for determining the risk of stent thrombosis. Each of the modules illustrated—encoding module 1200, storage 1300, classification module 1400 and training module 1500—operate on a computer, such as CPU 410 or computers on the internet 420, and include computer readable instructions, which may be encoded on a non-transient machine readable medium. FIG. 14 illustrates input files 1100 provided to the encoding module 1200 as illustrated by flow line 1010. In an exemplary embodiment input files the user interface 500 as illustrated in FIGS. 5-8 operates as the encoding module 1200 in order to place the data regarding the patient to be studied in the form represented by, e.g., data files 920, 930, 940, 950 and 960 illustrated in FIGS. 9-13. The output of the encoding module 1200 can be stored in storage 1330 as illustrated by flow line 1020.

The classification module 1400 takes an encoded file (e.g., files 920, 930, 940, 950) as input and determines the risk of stent thrombosis, e.g., early, late or very late. In an exemplary embodiment, the classification module 1400 includes the neural network described herein. The classification module 1400 may receive encoded data directly from the encoding module 1200 as illustrated by flow line 1030 or from storage 1300 by flow line 1050.

The training module 1500 trains the classification module 1400 using encoded data received either directly from the encoding module 1200 as illustrated by flow line 1040 or from storage 1300 by flow line 1060. In some embodiments, the training module 1500 performs training of the neural network as described herein above. In some embodiments, the training module 1500 directly modifies the classification module 1400 as training data is presented to it. In some embodiments, the training module 1500 determines the weights associated with connections between the input layer and the hidden layer and between the hidden layer and the output layer based on an entire set of training data and then provides these weights to the classification module 1400 as illustrated by flow line 1070.

To execute the functions represented above and illustrated in FIG. 14, a non-transient computer readable medium can be provided, which includes instructions for receiving one or more variables, the one or more variables comprising a baseline variable associated with a characteristic of a subject; instructions for calculating a risk factor associated with stent thrombosis in the subject based on the one or more variables; and instructions for providing an output relating to the risk factor.

In some embodiments, certain parameters, such as, e.g., discontinuation of thienopyridine <six months, LVEF <30%, prior renal insufficiency history, target lesion length ≥22 mm, in stent restenosis, multiple stents implanted, lesion class B2/C, prior coronary artery bypass surgery, multi-vessel disease and multi-lesion intervention may be considered strong predictors after training has been completed and granted greater weight.

The output from output layer is compared to the known incidence of ST. If the output of output layer does not indicate the expected probability of ST, a correction is calculated and applied to the parameters of the neural network. As an example, if the output indicated a value of 0 for "high risk of early ST" and 1 for "low risk of early ST" when predictors of high incidence of early ST were observed, a correction would be determined so that the next time such predictors were provided as input, the output would more accurately reflect the risk of early ST. In one embodiment, backpropagation as known in the art is used to train the neural network, and corrections are applied to the weights associated with the connections between the input layer and the hidden layer and between the hidden layer and the output layer. However, one of skill in the art would recognize that various other training methods known in the art could be substituted while still achieving the results of the present disclosure.

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and device of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method of predicting risk of stent thrombosis comprising:
   receiving, by one or more processors, an input value of a baseline angiographic variable associated with a subject before a stent implantation in the subject;
   determining, by the one or more processors, a probability score representing a risk of stent thrombosis in the subject based on the input value of the baseline angiographic variable to allow a physician to assess the risk of stent thrombosis in the subject before the stent implantation, wherein the baseline angiographic variable represents a parameter of a target vessel;
   performing the stent implantation, wherein the stent implantation includes selecting a stent based on the probability score, and implanting the stent in the target vessel of the subject, and wherein the stent is selected from a group including a bare metal stent or a drug eluting stent;
   determining an anti-platelet medication regimen for the subject based on the probability score, wherein the anti-platelet medication regimen includes a dual anti-platelet therapy type and a duration after the stent implantation;
   receiving, by the one or more processors, an input value of a post-procedural variable indicating that the anti-platelet medication regimen is discontinued prior to the duration after the stent implantation; and
   updating, by the one or more processors, the probability score based on the input value of the post-procedural variable to allow the physician to assess the risk of stent thrombosis in the subject after the stent implantation.

2. The method of claim 1, wherein determining the probability score representing the risk of stent thrombosis in the subject comprises calculating a risk associated with at least one of early stent thrombosis, late stent thrombosis, or very late stent thrombosis.

3. The method of claim 1, wherein determining the probability score representing the risk of stent thrombosis in the subject comprises encoding a digital file as a series of variables; and
   further comprising storing, by the one or more processors, the series of variables in a machine readable medium.

4. The method of claim 3 further comprising:
   classifying, by the one or more processors, the series of variables as predicting a level of risk of stent thrombosis; and
   providing, by the one or more processors, output indicative of the classification.

5. The method of claim 3 further comprising:
   receiving, by the one or more processors, a plurality of training series of variables with known risks of stent thrombosis; and
   modifying, by the one or more processors, a classification module to classify each of the training series of variables according to the known risk of stent thrombosis.

6. The method of claim 1 further comprising receiving, by the one or more processors, input values of one or more baseline demographic variables.

7. The method of claim 6, wherein the one or more baseline demographic variables comprises one or more variables selected from the group consisting of age; gender; current tobacco usage; diabetes-related drug intake; hypertension-related drug intake; dyslipidemia-related drug intake; Coronary Artery Bypass Graft history; percutaneous coronary intervention history; CCS III or IV; MI history; brachytherapy history; Acute Myocardial Infarction history; Renal Insufficiency history; Stroke history; Left Ventricle Ejection Fraction; and Number of Diseased Vessels.

8. The method of claim 1, wherein the baseline angiographic variable used by the one or more processors to determine the probability score includes a variable selected from the group consisting of target vessel; presence of thrombus; degree of calcification; pre-procedure RVD; pre-procedure DS %; pre-procedure TIMI; target lesion length; presence of in-stent restenosis; bifurcation; ostial; and ACC/AHA lesion class.

9. The method of claim 1 further comprising receiving, by the one or more processors, input values of one or more procedural variables associated with the stent implantation.

10. The method of claim 9, wherein the one or more procedural variables comprises one or more variables selected from the group consisting of drug eluting stent type; use of pre dilation; use of post dilatation; maximum balloon pressure; number of treated lesions; number of treated vessels; number of stents implanted; total length stent; bailout stent usage; and DAPT loading dose usage.

11. The method of claim 1, wherein the post-procedural variable includes a non-aspirin DAPT discontinuation event or an aspirin discontinuation event.

12. The method of claim 1, wherein the post-procedural variable includes a $P2Y_{12}$ receptor inhibitor discontinuation event or an aspirin discontinuation event.

13. A non-transient computer readable medium storing instructions, which when executed by one or more processors of a data processing system, cause the data processing system to perform a method comprising:
   training a neural network of a risk assessment model stored in a memory of a data processing system, wherein the neural network is trained using data regarding incidence of stent thrombosis among patients and associated information about the patients to determine weight associated with connections between an input layer, a hidden layer, and an output layer of the neural network;

receiving, by one or more processors of a data processing system, an input value of a baseline angiographic variable associated with a subject before a stent implantation in the subject;

determining, by the one or more processors using the risk assessment model, a probability score representing a risk of stent thrombosis in the subject based on the input value of the baseline angiographic variable to allow a physician to assess the risk of stent thrombosis in the subject before a stent implantation, wherein the baseline angiographic variable represents a parameter of a target vessel, and wherein determining the probability score includes providing the input value of the baseline angiographic variable to the input layer of the trained neural network, transmitting the input value of the baseline angiographic variable from the input layer to the hidden layer of the trained neural network, and obtaining the probability score from the output layer of the trained neural network;

providing, on a display of the data processing system, the probability score, wherein the probability score is for use by the physician to select a stent for the stent implantation based on the probability score, wherein the stent is selected from a group including a bare metal stent or a drug eluting stent for implantation in the target vessel of the subject, wherein the probability score is for use by the physician to determine an anti-platelet medication regimen for the subject based on the probability score, and wherein the anti-platelet medication regimen includes a dual anti-platelet therapy type and a duration after the stent implantation;

receiving, by the one or more processors, an input value of a post-procedural variable indicating that the anti-platelet medication regimen is discontinued prior to the duration after the stent implantation; and updating, by the one or more processors using the risk assessment model, the probability score based on the input value of the post-procedural variable to allow the physician to assess the risk of stent thrombosis in the subject after the stent implantation.

\* \* \* \* \*